United States Patent
Grosman et al.

(10) Patent No.: US 11,904,139 B2
(45) Date of Patent: Feb. 20, 2024

(54) CLOSED-LOOP CONTROL IN STEADY-STATE CONDITIONS

(71) Applicant: Medtronic MiniMed, Inc., Northridge, CA (US)

(72) Inventors: Benyamin Grosman, Winnetka, CA (US); Louis J. Lintereur, Boise, ID (US); Anirban Roy, Agoura Hills, CA (US); Neha J. Parikh, West Hills, CA (US); Di Wu, Glendale, CA (US); Patrick E. Weydt, Moorpark, CA (US); David Dunleavy, West Hills, CA (US); Ali Dianaty, Porter Ranch, CA (US)

(73) Assignee: Medtronic MiniMed, Inc., Northridge, CA (US)

(*) Notice: Subject to any disclaimer, the term of this patent is extended or adjusted under 35 U.S.C. 154(b) by 500 days.

(21) Appl. No.: 17/222,570

(22) Filed: Apr. 5, 2021

(65) Prior Publication Data

US 2022/0313908 A1    Oct. 6, 2022

(51) Int. Cl.
*A61M 5/172* (2006.01)

(52) U.S. Cl.
CPC ....... *A61M 5/1723* (2013.01); *A61M 2205/52* (2013.01); *A61M 2230/201* (2013.01)

(58) Field of Classification Search
CPC .... A61M 2005/14208; A61M 2205/52; A61M 2230/201; A61M 5/14244; A61M 5/1723; A61M 2205/50
See application file for complete search history.

(56) References Cited

U.S. PATENT DOCUMENTS

| | | | |
|---|---|---|---|
| 4,562,751 A | 1/1986 | Nason et al. | |
| 4,685,903 A | 8/1987 | Cable et al. | |
| 5,080,653 A | 1/1992 | Voss et al. | |
| 5,097,122 A | 3/1992 | Colman et al. | |
| 5,505,709 A | 4/1996 | Funderburk et al. | |
| 6,088,608 A | 7/2000 | Schulman et al. | |
| 6,119,028 A | 9/2000 | Schulman et al. | |
| 6,485,465 B2 | 11/2002 | Moberg et al. | |
| 6,554,798 B1* | 4/2003 | Mann | A61M 5/172 |
| | | | 604/67 |
| 6,558,320 B1 | 5/2003 | Causey, III et al. | |
| 6,558,351 B1 | 5/2003 | Steil et al. | |
| 6,562,001 B2* | 5/2003 | Lebel | G16H 20/17 |
| | | | 604/67 |

(Continued)

*Primary Examiner* — Quynh-Nhu H. Vu
(74) *Attorney, Agent, or Firm* — Weaver Austin Villeneuve & Sampson LLP

(57) ABSTRACT

A processor-implemented method for closed-loop control in steady-state conditions includes determining, based on data including historical bolus information but excluding historical basal information, an amount of unmetabolized therapeutic substance in a patient; determining, based on a difference between a most recent measurement of a physiological condition of the patient and a target value for the physiological condition, a first amount or rate of a basal dosage for delivery to the patient; adjusting, based on the amount of unmetabolized therapeutic substance, the first amount or rate of the basal dosage to determine a second amount or rate of the basal dosage; and causing delivery of the second amount or rate of the basal dosage based on communicating the second amount or rate in a delivery command.

20 Claims, 4 Drawing Sheets

(56) References Cited

U.S. PATENT DOCUMENTS

| | | |
|---|---|---|
| 6,589,229 B1 | 7/2003 | Connelly et al. |
| 6,641,533 B2 | 11/2003 | Causey, III et al. |
| 6,659,980 B2 | 12/2003 | Moberg et al. |
| 6,740,072 B2 | 5/2004 | Starkweather et al. |
| 6,744,350 B2 * | 6/2004 | Blomquist ............ A61M 5/142 604/890.1 |
| 6,752,787 B1 | 6/2004 | Causey, III et al. |
| 6,817,990 B2 | 11/2004 | Yap et al. |
| 6,827,702 B2 | 12/2004 | Lebel et al. |
| 6,932,584 B2 | 8/2005 | Gray et al. |
| 6,936,029 B2 * | 8/2005 | Mann ................ A61M 5/14244 604/500 |
| 7,204,823 B2 * | 4/2007 | Estes .................. A61M 5/1723 604/65 |
| 7,323,142 B2 | 1/2008 | Pendo et al. |
| 7,402,153 B2 | 7/2008 | Steil et al. |
| 7,515,060 B2 * | 4/2009 | Blomquist ........ A61M 5/14566 340/5.91 |
| 7,621,893 B2 | 11/2009 | Moberg et al. |
| 8,012,119 B2 * | 9/2011 | Estes .................... A61M 5/172 604/65 |
| 8,905,965 B2 * | 12/2014 | Mandro ............... G05D 7/0676 604/67 |
| 9,364,609 B2 * | 6/2016 | Keenan ................. A61M 5/172 |
| 10,275,573 B2 * | 4/2019 | Mazlish ................. G16H 20/60 |
| 10,449,298 B2 * | 10/2019 | Roy ........................ A61M 5/24 |
| 10,610,644 B2 * | 4/2020 | Mazlish ............. A61M 5/1723 |
| 11,565,043 B2 * | 1/2023 | O'Connor ......... A61M 5/14244 |
| 2014/0066887 A1 | 3/2014 | Mastrototaro et al. |
| 2014/0066889 A1 | 3/2014 | Grosman et al. |

* cited by examiner

CLOSED-LOOP CONTROL IN STEADY-STATE CONDITIONS

TECHNICAL FIELD

The disclosure is generally related to methods and devices for delivering therapy to a patient, such as insulin for diabetes therapy.

BACKGROUND

A patient may use insulin therapy to manage type I or type II diabetes. Insulin therapy may include use of insulin infusion systems for delivering or dispensing insulin. An insulin infusion system may include an infusion device which typically includes a small motor and drive train components configured to deliver insulin from a reservoir into the body of the patient, e.g., via a percutaneous needle or a cannula placed in the subcutaneous tissue. Insulin infusion systems may facilitate management of diabetes for some patients.

SUMMARY

The present disclosure relates to techniques for closed-loop control in steady-state conditions. The techniques may be practiced using systems; processor-implemented methods; and non-transitory processor-readable storage media storing instructions which, when executed by one or more processors, cause performance of closed-loop control in steady state conditions.

A processor-implemented method for closed-loop control in steady-state conditions, that includes determining, based on data including historical bolus information but excluding historical basal information, an amount of unmetabolized therapeutic substance in a patient; determining, based on a difference between a most recent measurement of a physiological condition of the patient and a target value for the physiological condition, a first amount or rate of a basal dosage for delivery to the patient; adjusting, based on the amount of unmetabolized therapeutic substance, the first amount or rate of the basal dosage to determine a second amount or rate of the basal dosage; and causing delivery of the second amount or rate of the basal dosage based on communicating the second amount or rate in a delivery command.

A system for closed-loop control in steady-state conditions that includes one or more processors and one or more processor-readable storage media. The one or more processor-readable storage media store instructions which, when executed by the one or more processors, cause performance of: determining, based on data including historical bolus information but excluding historical basal information, an amount of unmetabolized therapeutic substance in a patient; determining, based on a difference between a most recent measurement of a physiological condition of the patient and a target value for the physiological condition, a first amount or rate of a basal dosage for delivery to the patient; adjusting, based on the amount of unmetabolized therapeutic substance, the first amount or rate of the basal dosage to determine a second amount or rate of the basal dosage; and causing delivery of the second amount or rate of the basal dosage based on communicating the second amount or rate in a delivery command.

One or more non-transitory processor-readable storage media storing instructions which, when executed by one or more processors, cause performance of determining, based on data including historical bolus information but excluding historical basal information, an amount of unmetabolized therapeutic substance in a patient; determining, based on a difference between a most recent measurement of a physiological condition of the patient and a target value for the physiological condition, a first amount or rate of a basal dosage for delivery to the patient; adjusting, based on the amount of unmetabolized therapeutic substance, the first amount or rate of the basal dosage to determine a second amount or rate of the basal dosage; and causing delivery of the second amount or rate of the basal dosage based on communicating the second amount or rate in a delivery command.

The details of one or more examples are set forth in the accompanying drawings and the description below. Other features, object, and advantages will be apparent from the description and drawings, and from the claims.

DETAILED DESCRIPTION

Figure 1:
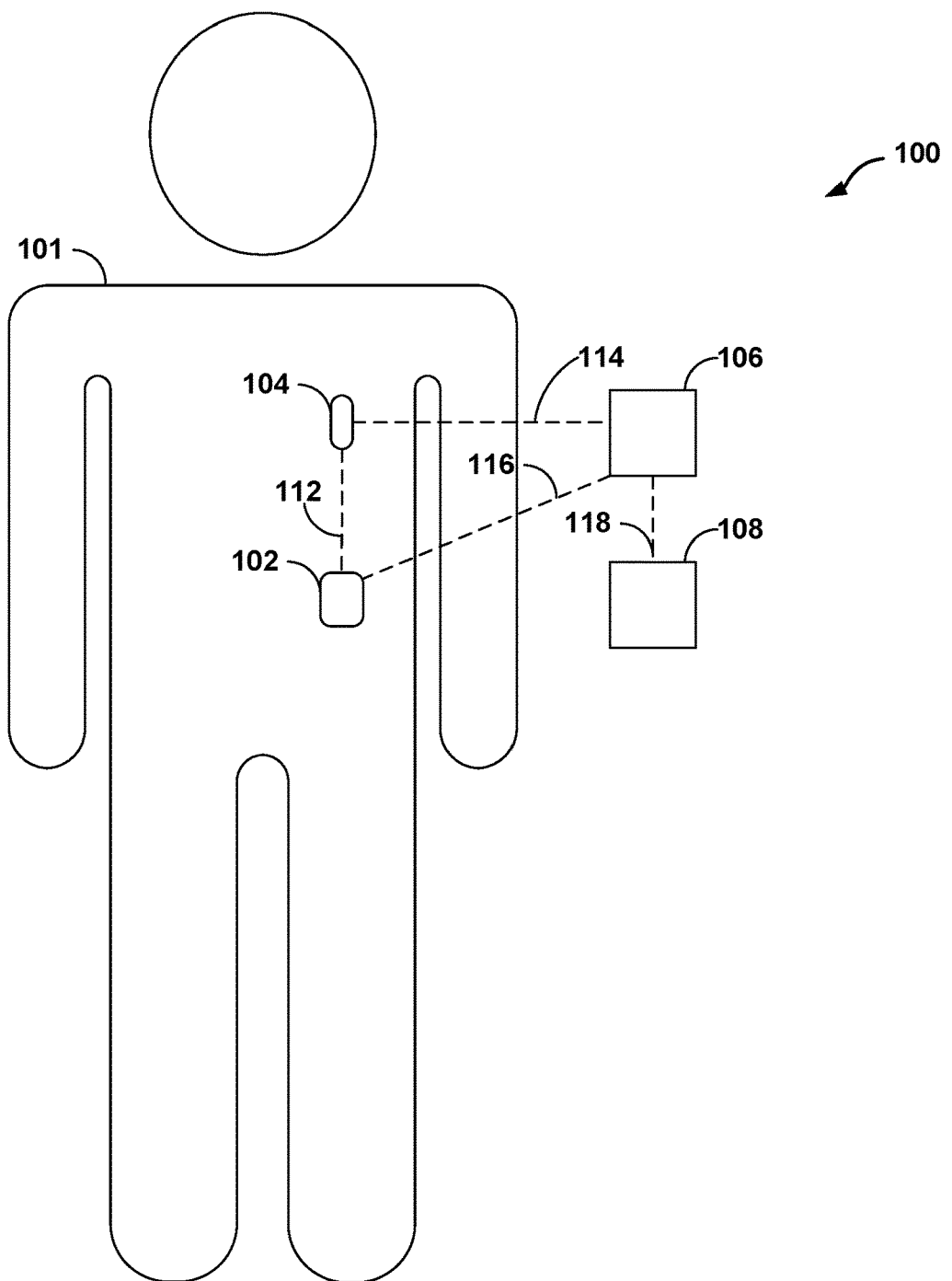
FIG. 1 is a conceptual diagram illustrating an example infusion system.

The present disclosure relates to systems and techniques for closed-loop control in steady-state conditions (e.g., when a patient's physiological condition is relatively stable within a healthy range). For the sake of clarity, the present disclosure provides examples in the diabetes context. However, it should be appreciated that the techniques disclosed herein are equally applicable outside the diabetes context (e.g., in pain management or other medical fields).

A healthy pancreas secretes relatively small amounts of insulin continuously throughout the day (e.g., between meals and during sleep). This is true even when a person is fasting or when a person's glucose level is stable within a euglycemic range. To emulate a healthy pancreas, some closed-loop control schemes are configured to cause an insulin delivery device to deliver basal dosages even in steady-state conditions.

For example, some closed-loop control schemes employ a proportional integral derivative (PID) controller to determine a potential basal dosage based on the difference between a patient's glucose level and a target glucose level. To avoid insulin stacking, the potential basal dosage can be offset by an estimate of any unmetabolized insulin that is represented by an insulin feedback (IFB) term. However, the IFB term typically accounts for any previously delivered bolus dosages as well as any previously delivered basal dosages. Thus, a basal dosage can be delivered when the amount of the potential basal dosage exceeds the amount of any unmetabolized insulin, which may even be attributable to a previously delivered basal dosage. Accommodating this interaction between the PID controller and the IFB term may involve a complicated system design that is imprecise.

To provide a simple illustration, the operation of the foregoing example can be examined under steady-state conditions (e.g., when the patient is fasting and the patient's glucose level is stable at a target value). If the patient's glucose level is stable at a target value, the proportional and derivative components of the PID controller would each produce a zero value. Thus, operation under steady-state conditions would be focused on the integral component and the IFB term. For the sake of simplicity, it is assumed that sufficient time has passed since any bolus dosage, so the IFB term may have a value of x corresponding to a previously delivered basal dosage. Accordingly, another basal dosage of x can be delivered when the integral component produces a value of 2x. Using an integral value of 2x to define when another basal dosage can be delivered may be less precise relative to a control scheme in which an integral value of less than 2x defines when another basal dosage can be delivered.

To address the aforementioned shortcomings, disclosed herein are techniques related to determining the amount or rate of a basal dosage based on excluding basal dosages from the calculation of unmetabolized insulin. In the example of a PID controller with an IFB term, the IFB term may be determined without historical basal information. This allows the IFB term to have a zero value in steady-state conditions. As a result, a basal dosage of x can be delivered when the integral term of the PID controller produces a value of x instead of an inflated value (e.g., 2x or some other multiple of x). This also allows the integral term to be limited to, e.g., clamped at, a value equal to a patient-specific maximum amount or rate of basal dosage, e.g., $U_{max}$. In this way, the techniques disclosed herein enable closed-loop control in a manner that increases safety and precision.

Although the techniques disclosed herein are explained in the context of insulin infusion systems, it should be appreciated that the disclosed techniques are not limited to insulin infusion systems. For example, the techniques may be implemented in an equivalent manner in the context of therapy delivery devices that are not configured for insulin infusion. Furthermore, it should be appreciated that the techniques disclosed herein can be practiced with one or more types of insulin (e.g., fast-acting insulin, intermediate-acting insulin, and/or slow-acting insulin). Thus, terms such as "basal insulin" and "bolus insulin" do not necessarily denote different types of insulin. For example, fast-acting insulin may be used for both basal dosages and bolus dosages.

FIG. 1 is a conceptual diagram illustrating an example infusion system 100. Infusion system 100 may be configured to deliver insulin to a patient 101 using a proportional integral derivative (PID) controller with an insulin feedback (IFB) term. Infusion system 100 may include infusion device 102, monitoring device 104, computing device 106, and user interface 108. Infusion device 102, monitoring device 104, computing device 106, and/or user interface 108 may be disposed on the same device, or on different devices. In some examples, infusion system 100, or one or more components thereof, may include a portable medical device and/or an implantable medical device. In some examples, infusion system 100 may include components similar to those described in, for example, commonly assigned U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893, each of which is incorporated herein by reference in its entirety.

Infusion device 102 is configured to deliver a therapeutic substance (e.g., insulin) to patient 101. Infusion device 102 may be secured to patient 101 (e.g., to the body or clothing of patient 101) or implanted in the body of patient 101. Infusion device 102 may be separate from or incorporated with one or more of monitoring device 104, computing device 106, and/or user interface 108.

In some examples, infusion device 102 may include a reservoir, an actuator, a delivery mechanism, and a cannula. The reservoir may be configured to store a predetermined amount of the therapeutic substance. In some examples, the reservoir may be refillable or replaceable. The actuator may be configured to drive the delivery mechanism. In some examples, the actuator may include a motor, such as an electric motor. The delivery mechanism may be configured to move insulin from the reservoir through the cannula. In some examples, the delivery mechanism may include a pump or a plunger. The cannula may facilitate a fluidic connection between the reservoir and the body of patient 101. In some examples, the cannula and/or a needle may facilitate delivery of the therapeutic substance to a tissue layer, vein, or body cavity of patient 101. In some examples, infusion device 102 may include additional components, such as a power supply and/or a transceiver for communication with other devices. During operation, the actuator, in response to a signal (e.g., a command signal), may drive the delivery mechanism, thereby causing the therapeutic substance to move from the reservoir, through the cannula, and into the body of patient 101.

Monitoring device 104 is configured to detect a physiological condition (e.g., a glucose concentration level) of patient 101. Monitoring device 104 may be secured to the body of patient 101 (e.g., to the skin of patient 101 via an adhesive) and/or at least partially implanted into the body of patient 101. Monitoring device 104 may be separate from or incorporated with infusion device 102, computing device 106, and/or user interface 108. Depending on the particular location or configuration, monitoring device 104 may be in contact with biological matter (e.g., interstitial fluid and/or blood) of patient 101. In some examples, monitoring device 104 may include one or more electrodes configured to generate a signal (e.g., a sensor data signal) indicative of a concentration of a biological marker, such as a glucose level of patient 101. In some examples, monitoring device 104 may be a continuous glucose monitoring device that senses glucose and communicates with one or more other devices such as infusion device 102 and/or computing device 106.

As illustrated in FIG. 1, monitoring device 104 may be communicatively coupled (e.g., connected) to computing device 106 via link 114 or infusion device 102 via link 112. Links 114 and 112 may each be any suitable wired or wireless connection. For example, monitoring device 104 may include a communications interface, such as an Ethernet card, a radio frequency transceiver, cellular transceiver, a Bluetooth® interface card, USB interface, and/or any other type of device that can send and/or receive information. Monitoring device 104 may generate a signal (e.g., output signal) representative of the physiological condition of patient 101, e.g., the concentration of the biological marker, and may provide the signal to computing device 106 via link 114 or infusion device 102 via link 112. In some examples, monitoring device 104 may be configured to condition the signal prior to providing the signal to computing device 106 or infusion device 102. Conditioning may include, but is not limited to, amplification, filtering, attenuation, isolation, and/or transformation. In some examples, monitoring device 104 may provide an unconditioned signal to computing device 106 or infusion device 102, either of which may condition the signal.

Monitoring device 104 may include an electrochemical sensor, an electrical sensor, and/or an optical sensor. In examples in which monitoring device 104 includes an electrochemical sensor, the electrochemical sensor may be configured to, in response to the interaction or binding of the biological marker to a substrate, generate an electronic signal based on a potential, conductance, and/or impedance of the substrate. The substrate may include a material selected to interact with a particular biomarker, such as glucose. The potential, conductance, and/or impedance may be proportional to a concentration of the particular biomarker.

In examples in which monitoring device 104 includes an electronic sensor, the electronic sensor may be configured to, in response to an electrical biosignal, generate an electronic signal based on an amplitude, frequency, and/or phase of the electrical biosignal. The electrical biosignal may include a change in electric current produced by the sum of an electrical potential difference across a tissue, such as the nervous system, of patient 101. In some examples, the electrical biosignal may include portions of a potential change produced by the heart of patient 101 over time, e.g., recorded as an electrocardiogram, that are indicative of a glucose level of patient 101.

In examples in which monitoring device 104 includes an optical sensor, the optical sensor may be configured to, in response to the interaction or binding of the biological marker to a substrate, generate an electronic signal based on change in luminance of the substrate. For example, the substrate may include a material selected to fluoresce in response to contact with a selected biomarker, such as glucose. The fluorescence may be proportional to a concentration of the selected biomarker.

Computing device 106 may be operatively coupled to infusion device 102 and/or monitoring device 104 to control operation of infusion device 102 and/or monitoring device 104. Computing device 106 may be secured to patient 101 (e.g., to the body or clothing of patient 101), at least partially implanted into the body of patient 101, or remotely located from patient 101. Computing device 106 may be separate from or incorporated with infusion device 102, monitoring device 104, and/or user interface 108.

Computing device 106 may be any suitable computing device, such as a smartphone, a computerized wearable device (e.g., a watch, eyewear, ring, or necklace), a tablet computer, a laptop computer, or a desktop computer. Computing device 106 may be a consumer device configured to perform the techniques of this disclosure by executing program instructions, and/or computing device 106 may be a special purpose device (e.g., a remote control device) provided by, for example, the manufacturer of infusion device 102. Computing device 106 may include various types of fixed function and/or programmable processing circuitry or other hardware, including, but not limited to, microprocessors, controllers, digital signal processors (DSPs), application specific integrated circuits (ASICs), field-programmable gate arrays (FPGAs), or equivalent discrete or integrated logic circuitry, as well as combinations of such components. The term "processing circuitry" may generally refer to any of the foregoing logic circuitry, alone or in combination with other logic circuitry, or any other equivalent circuitry. In some examples, computing device 106 includes hardware that can be configured to execute firmware and/or software that sets forth one or more of the techniques described herein. For example, computing device 106 may be configured to implement functionality, process instructions, or both for execution of processing instructions stored within one or more storage components.

In some examples, sensor data from monitoring device 104 is received by processing circuitry of computing device 106. The processing circuitry may condition (or further condition) the received sensor data, for example, as described above.

In some examples, computing device 106 may be configured to receive user input, e.g., a meal indication, via user interface 108. An example meal indication may include a type of meal (e.g., breakfast, lunch, dinner, snack, or other meal), an approximate amount of carbohydrates consumed/to be consumed, and/or other information that may affect an amount of insulin to be delivered as a meal bolus. In response to receiving the user input, the processing circuitry of computing device 106 may determine a meal bolus amount. The meal bolus amount may be an amount of insulin that is sufficient for counteracting an increase in glucose level caused by consumption of a meal (e.g., a certain amount of carbohydrates).

In some examples, computing device 106 is operatively coupled (e.g., connected) to infusion device 102 via link 116. Link 116 may be the same or similar to link 114 discussed above. Thus, computing device 106 may control operation of infusion device 102 via link 116. For example, computing device 106 may generate one or more signals (e.g., a command signal) that cause infusion device 102 to deliver insulin to patient 101, e.g., as a basal dosage and/or a bolus dosage.

In some examples, computing device 106 may receive from infusion device 102 data associated with insulin delivery (e.g., insulin delivery data). Insulin delivery data may include, but is not limited to, a type of insulin being delivered, historical insulin delivery rates and/or amounts, current insulin delivery rate and/or amount, and/or user input affecting insulin delivery. In some examples, the insulin delivery data is received by processing circuitry of computing device 106. The processing circuitry of computing device 106 (and/or processing circuitry of one or more other devices of infusion system 100) may determine a predicted change in concentration of the biological marker, e.g., a glucose level, based on the insulin delivery data.

Computing device 106 may be operatively coupled (e.g., connected) to user interface 108 (e.g., via link 118 or some other wired or wireless connection if user interface 108 is implemented on a separate device from computing device 106). In some examples, computing device 106 and user interface 108 may be integrated into a single device, such as a smart phone, tablet computer, laptop computer, or the like. User interface 108 may be a graphical user interface (GUI) and/or may be implemented using a display device, a keyboard, a touchscreen, a speaker, a microphone, a gyroscope, an accelerometer, a vibration motor, and/or the like. Computing device 106 may generate information that is communicated to a user (e.g., patient 101, a caregiver, or a clinician) via user interface 108 as tactile output, audio output, video output, or the like. In this way, user interface 108 may notify a user of sensor data (e.g., a glucose level) and/or insulin delivery data (e.g., rates of historic, current, or future insulin delivery). As one example, computing device 106 may receive an indication of a change in insulin delivery from infusion device 102 and cause user interface 108 to present an alert indicative of the change in insulin delivery. The alert may include any type of information understandable by a human. For example, the alert may include information representative of the change in insulin delivery that can be displayed on a display device of user interface 108. In some examples, the display device of user interface 108 may be included in a mobile device of the user, and the information representative of the change in insulin delivery may be a text, email, system notification, push notification, or web application notification.

In some examples, computing device 106 may receive tactile input, kinetic input, audio input, optical input, or the like from a user via user interface 108. Thus, user interface 108 may receive user input from a user and send the user input to computing device 106. The user input (e.g., user data) may include, for example, a requested change in insulin delivery, a glucose level, and a meal indication.

In some examples, infusion device 102, monitoring device 104, and computing device 106 are configured to utilize a closed-loop control system for delivering insulin to patient 101. Example insulin infusion systems and techniques using closed-loop control systems may include, but are not limited to, the systems and techniques described in U.S. Pat. Nos. 6,088,608, 6,119,028, 6,589,229, 6,740,072, 6,827,702, 7,323,142, and 7,402,153 or United States Patent Application Publication Nos.: 2014/0066887 and 2014/0066889, all of which are incorporated herein by reference in their entirety. For example, monitoring device 104 may be configured to detect a condition of the patient, such as a glucose level. Infusion device 102 may be configured to deliver insulin to patient 101 based on the detected condition. Monitoring device 104 may continue to detect a condition of patient 101, thereby providing infusion device 102 with feedback data to continuously or periodically adjust a rate of insulin delivery in an automatic or autonomous manner based on the feedback data. In some examples, infusion device 102, monitoring device 104, and computing device 106 may be configured to utilize the closed-loop system only for a portion of the day, for example only when the patient is asleep or awake.

During operation, in some examples, computing device 106 may determine dosage commands that govern operation of infusion device 102. The dosage commands may include, but are not limited to, commands for delivering a basal dosage and/or a bolus dosage. An example basal dosage is an amount of insulin delivered to patient 101 to maintain glucose levels during periods of fasting, and an example bolus dosage is an amount of insulin (e.g., a meal bolus) delivered to patient 101 to regulate a rapid increase in glucose levels caused by consumption of a meal.

In some examples, the dosage commands may be based on patient-specific data. Examples of patient-specific data may include an insulin sensitivity factor, an active insulin time, and an insulin-to-carbohydrate ratio.

As will be described in greater detail below, in a closed-loop operating mode, computing device 106 may determine dosage commands based on a difference between a current (e.g., most recently measured) glucose level in the body of the patient (e.g., received from monitoring device 104) and a target glucose level (e.g., determined by computing device 106). In this regard, the rate of insulin delivery may be related to the difference between the current glucose level and the target glucose level.

In some examples, computing device 106 is configured to determine an insulin delivery command to cause delivery of a basal dosage and/or a bolus dosage. The insulin delivery command may be modified, at least in part, by an insulin feedback (IFB) term of a closed-loop glucose control scheme. For example, the IFB term may be subtracted from an uncompensated delivery command, and the resulting output (e.g., a bolus compensated delivery command) may be communicated to infusion device 102.

The IFB term may include a numeric value that accounts for the amount of insulin that has yet to be metabolized (e.g., insulin on-board (IOB)). The IOB, or active insulin or bolus on-board, may include an amount, such as a number of units, of rapid-acting insulin that is still working. In some examples, computing device 106 may be configured to determine the IFB term based on the total amount of insulin, excluding basal dosages, delivered over a predetermined duration, less an insulin metabolism amount for the duration. The insulin metabolism amount may be based on known pharmacodynamics curves for rapid-acting insulin.

Additionally, because the IFB term excludes basal dosages, the integral component of the closed-loop control scheme may be limited to a value equal to a maximum amount or rate of basal dosage, e.g., $U_{max}$, for the particular patient. In contrast, if the IFB term included basal dosages, the integral component would be limited to double that value (e.g., $2*U_{max}$). Limiting the integral component to $U_{max}$ instead of $2*U_{max}$ may simplify control of integral windup.

In some examples, the IFB term may be determined based on user input. For example, the patient may input an adjustment to a rate of insulin metabolism used to determine the IFB term. The adjustment may include a proportion (e.g., a fraction or a percentage) or a discrete value. The adjustment may reflect the patient's experience with hypoglycemia or hyperglycemia following a bolus delivery or basal delivery. In some examples, computing device 106 may be configured to track patient adjustments to the rate of insulin metabolism. By enabling user input to adjust a rate of insulin metabolism, and tracking such adjustments, computing device 106 may learn to automatically make similar adjustments.

In some examples, the IFB term of the closed-loop control process may cause infusion device 102 to automatically reduce (e.g., suspend) basal delivery. By accounting for IOB in the IFB term, the probability of insulin stacking may be reduced (e.g., to zero) so as to curtail or avoid over-delivery of insulin.

In some examples, computing device 106 may determine, based on a mathematical model, a probability metric representing the likelihood of a hypoglycemic event following delivery of the augmented bolus and automatically cause reduction of basal dosage deliveries for a postprandial duration of time that is influenced by the probability metric. For example, computing device 106 may cause infusion device 102 to reduce basal dosage deliveries until the probability of the hypoglycemic event is less than a threshold value, at which time computing device 106 may cause infusion device 102 to increase basal dosage deliveries.

As described herein, the bolus dosage of insulin delivered in connection with a meal may be automatically increased or otherwise adjusted while the infusion device is in an automated or autonomous operating mode to reduce the postprandial peak or rate of increase in the patient's glucose levels. Additionally, basal dosage deliveries in the autonomous operating mode may be automatically reduced for at least an initial portion of the postprandial period, thereby reducing the likelihood of potential over-delivery or postprandial hypoglycemia. Thus, the postprandial glycemic peak is reduced while also reducing the likelihood of postprandial hypoglycemia.

Although described as delivering insulin, in other examples, infusion system 100 may be configured to deliver one or more other fluid, liquids, gels, or medications to patient 101. Example fluids, liquids, gels may include, but are not limited to, a nutritional supplement, a dye, a tracing medium, a saline medium, a hydration medium, or the like. Example medications may include, but are not limited to, HIV drugs, drugs to treat pulmonary hypertension, iron chelation drugs, pain medications, anti-cancer treatments, vitamins, hormones, or the like.

Figure 2:
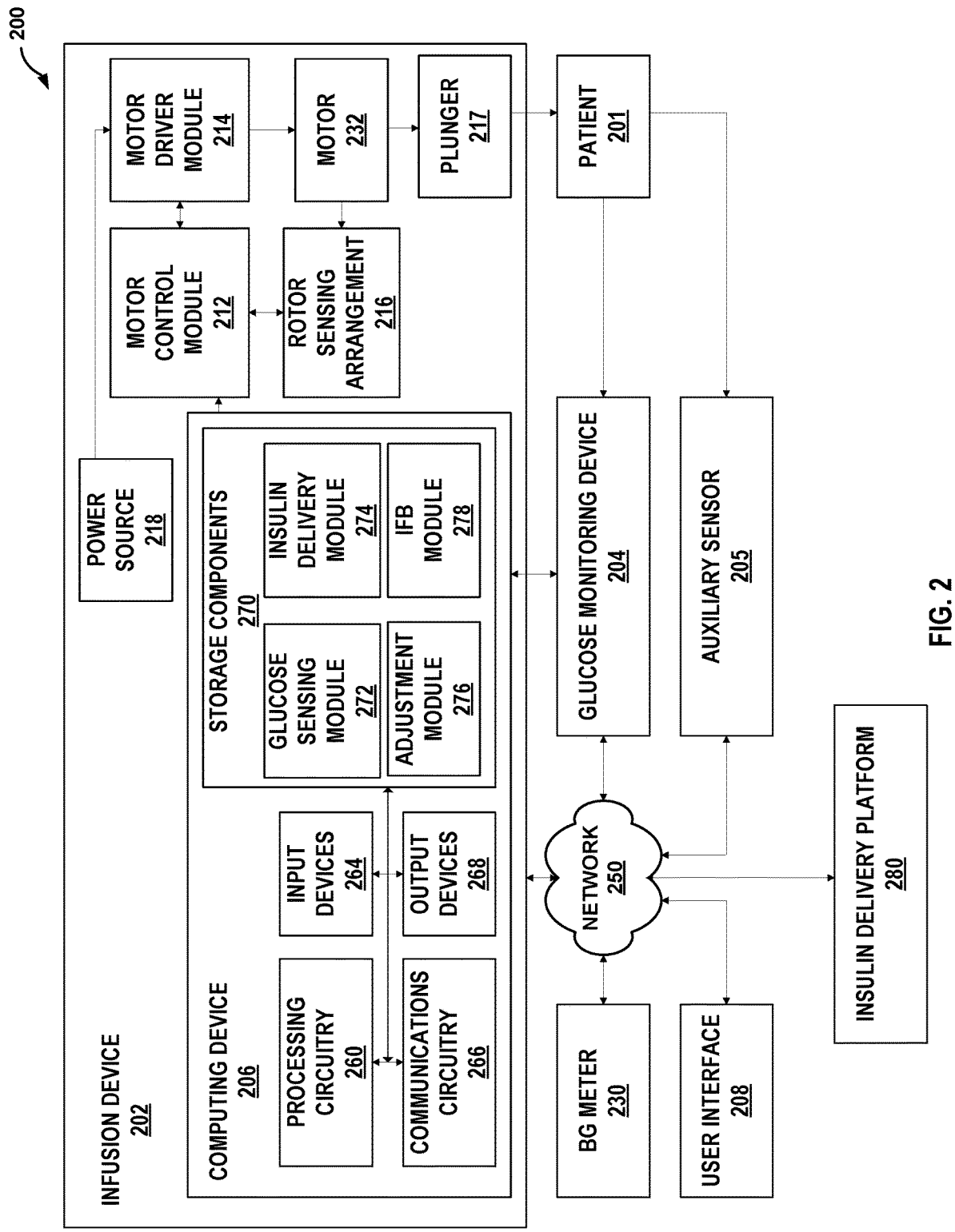
FIG. 2 is a schematic diagram illustrating an example of an insulin infusion system.

FIG. 2 depicts an example insulin infusion system 200 suitable for use with an infusion device 202, such as the infusion device 102 described above. Insulin infusion system 200 is configured to regulate a physiological condition in patient 201 toward a desired value (e.g. target value) or otherwise maintain the physiological condition within a desired range of values in an automated or an autonomous manner. Insulin infusion system 200 may be the same or substantially similar to infusion system 100 described in reference to FIG. 1, except for the differences described herein. For example, like infusion system 100, insulin infusion system 200 includes an infusion device, a glucose monitoring device, a computing device, and a user interface.

As illustrated in FIG. 2, infusion device 202 may be integrated with computing device 206. Each of infusion device 202 (e.g., including computing device 206), glucose monitoring device 204, and user interface 208 is optionally coupled to network 250. In some examples, fewer components (e.g., only computing device 206) may be coupled to network 250. Network 250 may include any public or private communication network, for instance, based on Bluetooth, WiFi®, a proprietary protocol for communicating with implantable medical devices, or other types of networks for transmitting data between computing systems, servers, and/or computing devices, both implanted within and located external to a patient. Infusion device 202 (e.g., including computing device 206), glucose monitoring device 204, and user interface 208 may each be communicatively coupled to network 250 using a respective network link, which may include any type of network connection, such as a wired or wireless connection. Network 250 may provide a device (e.g., infusion device 202, computing device 206, glucose monitoring device 204, and/or other components of system 200) with access to the Internet and/or may allow devices to communicate with each other.

Computing device 206 is configured to control operation of the insulin infusion device 202 according to one or more infusion delivery programs. Computing device 206 may include processing circuitry 260, one or more input devices 264, communications circuitry 266, one or more output devices 268, and one or more storage components 270. In some examples, computing device 206 maintains sets of instructions in the one or more storage components 270 (e.g., glucose sensing module 272, insulin delivery module 274, adjustment module 276, and IFB module 278). In some examples, computing device 206 may include additional components or fewer components.

Processing circuitry 260 may include various types of hardware, including, but not limited to, one or more microprocessors, controllers, digital signal processors (DSPs), application specific integrated circuits (ASICs), field-programmable gate arrays (FPGAs), or equivalent discrete or integrated logic circuitry, as well as combinations of such components. The terms "processing circuitry" or "processors" may generally refer to any of the foregoing logic circuitry, alone or in combination with other logic circuitry, or any other equivalent circuitry. Processing circuitry 260 represents hardware that can be configured to execute firmware and/or software that sets forth one or more of the algorithms described herein. For example, processing circuitry 260 may be configured to implement functionality, process instructions, or both. In some examples, processing circuitry 260 may be configured to execute sets of instructions stored within one or more storage components 270. Examples of such sets of instructions include glucose sensing module 272, insulin delivery module 274, adjustment module 276, and IFB module 278. In some examples, processing circuitry 260 includes processing circuitry of an implantable medical device and/or other devices of system 200 (e.g., infusion device 202, glucose monitoring device 204, or the like).

Computing device 206 also includes one or more input devices 264. Input devices 264, in some examples, are configured to receive input from a user through tactile, audio, or video sources. Examples of input devices 264 include a mouse, a button, a keyboard, a voice responsive system, video camera, microphone, touchscreen, or any other type of device capable of detecting a command from a user. In some example approaches, user interface 208 includes all input devices 264 employed by computing device 206.

Computing device 206 further includes communications circuitry 266. Computing device 206 may utilize communications circuitry 266 to communicate with external devices (e.g., glucose monitoring device 204, auxiliary sensors 205, user interface 208, and/or blood glucose meter 230) via network 250 and/or one or more wired or wireless networks. Communications circuitry 266 may include a communications interface, such as an Ethernet card, a radio frequency transceiver, cellular transceiver, a Bluetooth® interface card, USB interface, or any other type of device that can send and/or receive information. In some examples, computing device 206 utilizes communications circuitry 266 to wirelessly communicate with an external device such as a remote server system (e.g., insulin delivery platform 280).

Computing device 206 may further include one or more output devices 268. Output devices 268, in some examples, are configured to provide output to a user, for example, using audio, video or tactile media. For example, output devices 268 may include user interface 208, a sound card, a video graphics adapter card, or any other type of device for converting a signal into an appropriate form understandable to humans. In some example approaches, user interface 208 includes all output devices 268 employed by computing device 206.

One or more storage components 270 may be configured to store information within computing device 206 during operation. One or more storage components 270, in some examples, include one or more non-transitory processor-readable storage media or processor-readable storage devices. In some examples, one or more storage components 270 include a temporary memory, meaning that a primary purpose of one or more storage components 270 is not long-term storage. One or more storage components 270, in some examples, include a volatile memory, meaning that one or more storage components 270 does not maintain stored contents when power is not provided to one or more storage components 270. Examples of volatile memories include random access memories (RAM), dynamic random-access memories (DRAM), static random-access memories (SRAM), and other forms of volatile memories known in the art. In some examples, one or more storage components 270 are used to store program instructions for execution by processing circuitry 260. One or more storage components 270, in some examples, are used by software or firmware applications running on computing device 206 to temporarily store information during program execution.

In some examples, one or more storage components 270 may further include one or more storage components configured for longer-term storage of information. In some examples, one or more storage components 270 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

As noted above, computing device 206 also may include glucose sensing module 272, insulin delivery module 274, adjustment module 276, and IFB module 278. Each of glucose sensing module 272, insulin delivery module 274, adjustment module 276, and IFB module 278 may be implemented in various ways. For example, glucose sensing module 272, insulin delivery module 274, adjustment module 276, and/or IFB module 278 may be implemented as an application or a part of an application executed by processing circuitry 260. In some examples, glucose sensing module 272, insulin delivery module 274, adjustment module 276, and/or IFB module 278 may be implemented as part of a hardware unit of computing device 206 (e.g., as circuitry).

Functions performed by glucose sensing module 272, insulin delivery module 274, adjustment module 276, and IFB module 278 are explained in further detail below, and in reference to the examples illustrated in FIGS. 3 and 4. In some examples, the features and/or functionality of the computing device 206, e.g., glucose sensing module 272 insulin delivery module 274, adjustment module 276, and/or IFB module 278, may be at least partially implemented by a remote computing device or server, e.g., insulin delivery platform 280, that is physically distinct and/or separate from the computing device 206.

In some examples, glucose monitoring device 204 includes one or more interstitial glucose sensing elements configured to output signals (e.g., electrical or optical signals) indicative of the interstitial fluid glucose level in patient 201. Glucose monitoring device 204 may filter or otherwise process the output signals to obtain values indicative of the interstitial fluid glucose level (e.g. sensor data). In some examples, glucose monitoring device 204 may be calibrated based on a measurement of blood glucose. For example, insulin infusion system 200 may include a blood glucose meter 230. Blood glucose meter 230 may include a device (e.g., a finger stick device) configured to obtain a blood sample. Computing device 206, or some other device that executes instructions such as those maintained as glucose sensing module 272, may be communicatively coupled to blood glucose meter 230 via network 250 and configured to use a blood glucose measurement as a reference glucose level for calibrating the glucose monitoring device 204. In this way, the reference glucose level and values indicative of the interstitial fluid glucose level may be used to determine a calibrated glucose level (e.g., a sensor glucose level or a sensed glucose level).

In some examples, insulin infusion system 200 may include at least one auxiliary sensor 205. Auxiliary sensor 205 may be worn, carried, or operatively coupled to patient 201 to measure activity or physiological parameters of the patient that may influence the glucose levels or glycemic response of patient 201. Auxiliary sensor 205 may be a standalone component worn by the patient and/or may be integrated with infusion device 202 or glucose monitoring device 204. In some examples, auxiliary sensor 205 may include a heart rate sensor configured to detect a heart rate of patient 201. The heart rate of patient 201 may be indicative of exercise that may influence the glucose level or glycemic response of patient 201. In some examples, auxiliary sensor 205 may include an acceleration sensor configured to detect an acceleration of patient 201. The acceleration (or lack thereof) may be indicative of exercise, sleep, or some other condition of patient 201 that may influence the glycemic response of patient 201. In some examples, auxiliary sensor 205 may include an invasive, interstitial, and/or subcutaneous sensor configured to be inserted into the patient 201 to obtain measurements of other physiological conditions, such as a lactate level, a ketone level, or the like.

In some examples, auxiliary sensor 205 may include one or more environmental sensors to detect the current operating environment around infusion device 202. For example, the environmental sensors may include a temperature sensor, a humidity sensor, and/or a pressure sensor. In some examples, auxiliary sensor 205 may include a position sensor to detect the current geographic location of infusion system 200, such as a global positioning system (GPS) receiver.

Infusion device 202 includes motor control module 212, which may be coupled via motor driver module 214 to motor 232 or some other actuator configured to provide insulin to patient 201, for example, based on displacing plunger 217 in a reservoir. Motor 232 may be any suitable electric motor, such as a direct current (DC) motor or a brushless DC motor. Motor driver module 214 is coupled to power source 218 and motor 232. Motor control module 212 is coupled to motor driver module 214. In response to receiving, from computing device 206, a dosage command indicative of an amount of insulin and/or a rate of insulin delivery, motor control module 212 may generate and output one or more signals that operate motor driver module 214 to provide current from power source 218 to motor 232 to displace plunger 217. The dosage command may be based on a selected infusion delivery program. In some examples, the dosage command may be indicative of a bolus, such as a meal bolus.

In examples in which computing device 206 is configured to control insulin infusion device 202 in a closed-loop mode, computing device 206, or some other device that executes instructions such as those maintained as glucose sensing module 272, may determine a current glucose level and a target glucose level. The current glucose level may be determined based on sensor data received from glucose monitoring device 204, auxiliary sensor 205, and/or blood glucose meter 230. Computing device 206, or some other device that executes instructions such as those maintained as glucose sensing module 272, may determine the target glucose based on an upper glucose limit (e.g., a hyperglycemic threshold), a lower glucose limit (e.g., a hypoglycemic threshold), and/or a range of glucose levels. In some examples, computing device 206, or some other device that executes instructions such as those maintained as glucose sensing module 272, may store the target value, the upper glucose limit, the lower glucose limit, and/or the range of glucose levels. After determining the current glucose level and the target glucose level, computing device 206, or some other device that executes instructions such as those maintained as insulin delivery module 274, may determine dosage commands for delivering insulin to patient 201. The dosage commands, e.g., indicative of an amount of insulin to be delivered and/or a rate of insulin delivery, enable regulating the current glucose level toward the target glucose level. In some examples, the dosage commands may be based on the difference between a current glucose level and the target glucose level. Additionally, or alternatively, the dosage commands may be indicative of a meal bolus amount that is determined based on a meal indication, such as user input indicative of an amount of carbohydrates in a meal or a predicted amount of carbohydrates in a meal based on meal modeling. In this way, infusion device 202 may be configured to determine, in response to a meal indication, a meal bolus.

In some examples, computing device 206 may be configured to determine, in response to a meal indication, an augmented meal bolus. For example, adjustment module 276 may cause automatic adjustment of an insulin-to-carbohydrate ratio such that an enlarge bolus dosage is determined for a meal.

In some examples, computing device 206 may be configured to determine a duration of a postprandial period of reduced basal dosage deliveries. For example, the duration may be determined based on historical durations of glycemic response to historical augmented meal boluses, such as durations for a glucose level or IOB to return to a target level after a meal.

During operation, in response to receiving an insulin delivery command from computing device 206 or some other device that executes instructions such as those maintained as insulin delivery module 274, motor control module 212 may determine a power level and a power supply duration. The power level and the power supply duration may be proportional to the amount of insulin to be delivered and/or the rate of insulin delivery. Motor driver module 214, in response to a signal indicative of the power level and the power supply duration, may deliver power from power source 218 to motor 232 at the determined power level and power supply duration. Motor 232 may drive plunger 217 to deliver to patient 201 the desired amount of insulin at the desired rate of insulin delivery.

Power source 218 may include any suitable power source. In some examples, power source 218 may include a rechargeable or non-rechargeable battery housed within infusion device 202. Power source 218 may be configured to provide direct current (DC) power. Motor driver module 214 may include any suitable combination of circuitry or hardware to convert the DC power into alternating current (AC) signals. The AC signals may be applied to respective phases of the stator windings of motor 232, thereby resulting in current flowing through the stator windings to generate a stator magnetic field and cause the rotor of motor 232 to rotate. For example, motor control module 212 may be configured to receive a dosage command from computing device 206, or some other device that executes instructions such as those maintained as insulin delivery module 274, to determine a commanded translational displacement of plunger 217, and to determine a rotation of motor 232 to achieve the commanded translational displacement of plunger 217. In some examples, motor control module 212 may determine, based on a current rotational position (e.g., orientation) of a rotor of motor 232 indicated by the output of rotor sensing arrangement 216, the appropriate sequence of AC signals to be applied to the respective phases of the stator windings to rotate the rotor by the desired amount of rotation from its current rotational position.

Motor control module 212 may include a general purpose processor, a microprocessor, a controller, a microcontroller, a state machine, a content addressable memory, an application specific integrated circuit, a field programmable gate array, any suitable fixed function or programmable logic device, discrete gate or transistor logic, discrete hardware components, or any combination thereof, designed to perform the functions described herein. In some examples, the motor control module 212 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory processor-readable medium, which is capable of storing programming instructions for execution by the motor control module 212. The processor-executable programming instructions, when read and executed by the motor control module 212, cause the motor control module 212 to perform or otherwise support the tasks, operations, functions, and processes described herein. In some examples, the features and/or functionality of the motor control module 212 may be implemented by or otherwise integrated into the computing device 206, or vice versa.

Figure 3:
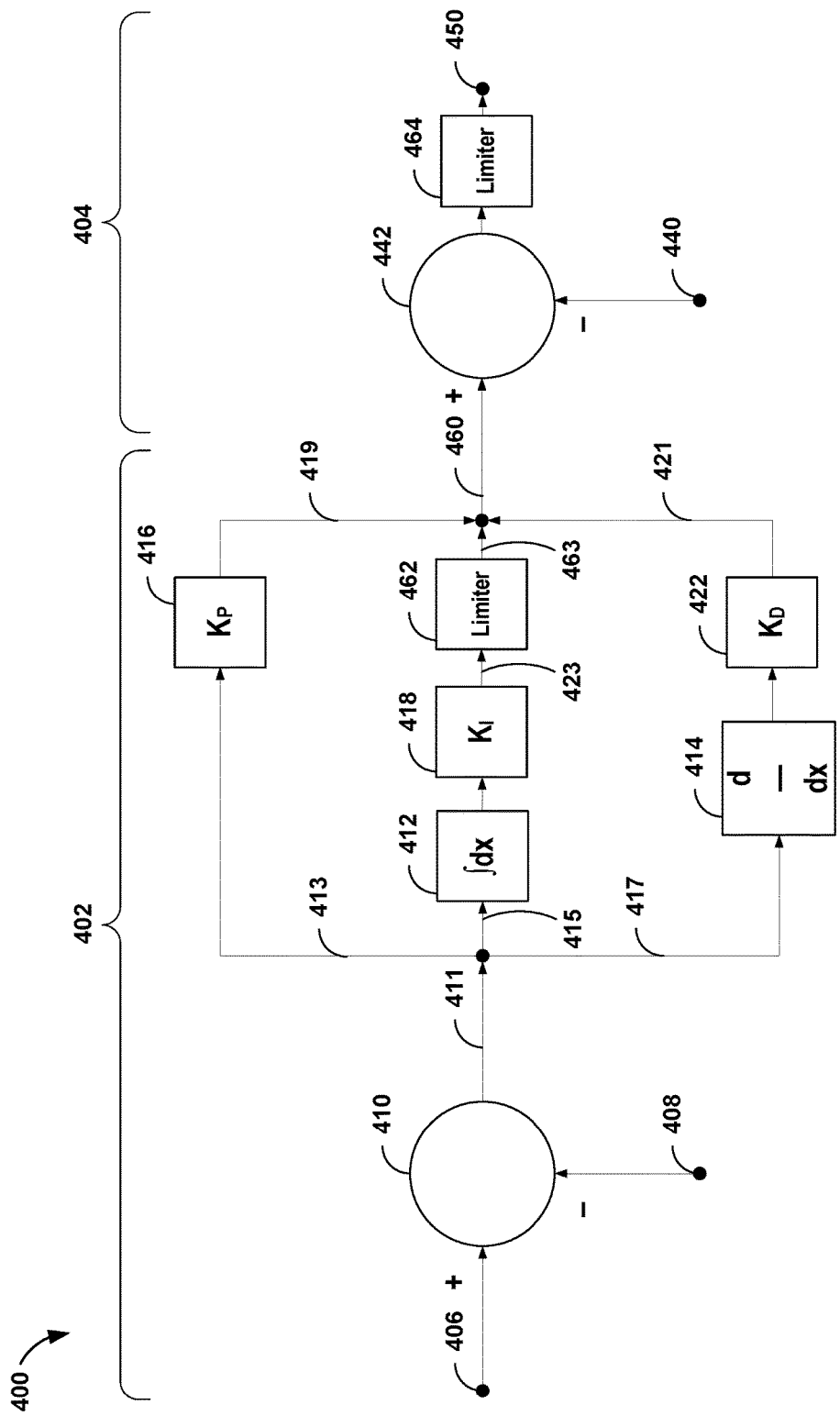
FIG. 3 is a schematic diagram illustrating an example closed-loop control system.

FIG. 3 is a schematic diagram illustrating an example closed-loop control system 400 that may be implemented by computing device 106 or 206, such as by execution of instructions maintained as one or more modules in storage components 270, to automatically or autonomously regulate a glucose level of a patient toward a target glucose level. Closed-loop control system 400 includes proportional-integral-derivative (PID) controller 402 that is configured to determine insulin delivery commands for operating motor 232 based at least in part on the difference between current glucose level 406 and target glucose level 408. In some examples, PID controller 402 operates to reduce (e.g., minimize) the difference (e.g. error) between current glucose level 406 and target glucose level 408. Closed-loop control system 400 also includes insulin feedback (IFB) portion 404 that adjusts PID delivery command 460 to compensate for bolus IOB. IFB portion 404 may exclude any basal dosages delivered by closed-loop control system 400.

PID controller 402 may take, as input, target glucose level 408. In some examples, glucose sensing module 272 may determine target glucose level 408 based on one or more patient-specific parameters. In some examples, PID controller 402 may obtain target glucose level 408 from an external device, such as insulin delivery platform 280. In some examples, computing device 206, or some other device that executes instructions such as those maintained as glucose sensing module 272, may store target glucose level 408. Additionally, PID controller 402 receives, as input, current glucose level 406, e.g., as provided by glucose monitoring device 204.

Closed-loop control system 400 includes summation block 410 configured to determine error term 411 which is equal to the difference between target glucose level 408 and current glucose level 406 (or vice versa). Error term 411 is provided to each of proportional term path 413, integral term path 415, and derivative term path 417. Within each of proportional term path 413, integral term path 415, and derivative term path 417, PID control parameters are applied to error term 411.

Proportional term path 413 includes gain block 416. In some examples, gain block 416 multiplies error term 411 by a proportional gain coefficient, $K_P$, to produce proportional term 419. The value of $K_P$ may affect the rate of error reduction, e.g., a larger $K_P$ may have a greater or more rapid effect on target glucose level 408 relative to a smaller $K_P$.

Derivative term path 417 includes derivative block 414 that determines the derivative of error term 411. The derivative of error term 411 may be indicative of a rate of change of error term 411 over time and, in some example, indicative of a future error in target glucose level 408. Alternatively, in some examples, derivative block 414 may determine the derivative of proportional term 419. In other words, proportional term 419 may be an input to derivative term path 417. Derivative term path 417 also includes gain block 422 that multiplies the derivative of error term 411 by a derivative gain coefficient, $K_D$, to produce derivative term 421.

Integral term path 415 includes integration block 412 that determines the integral of error term 411. The integral of error term 411 may be indicative of the sum of past error terms. Integral term path 415 includes gain block 418 that multiplies the integrated error term by an integral gain coefficient, $K_I$, to produce integral term 423. Alternatively, in some examples, integration block 412 may determine the integral of proportional term 419. In other words, proportional term 419 may be an input to integral term path 415.

In the example of FIG. 3, integral term path 415 includes limiter 462. Limiter 462 may be configured to apply one or both of an upper limit and lower limit to integral term 423. For example, the upper limit may be equal to $U_{max}$, and the lower limit may be equal to a safe basal rate (e.g., a patient-specific minimum basal rate determined based on dividing the patient's mean/median total daily dose by 48).

The output of limiter 462 is constrained integral term 463. Proportional term 419, constrained integral term 463, and derivative term 421 may be added or otherwise combined to produce PID delivery command 460 (e.g., an uncompensated delivery command). The PID delivery command 460 may specify a basal delivery value that has been rounded or truncated to a pump delivery resolution, e.g., an increment of 0.025 units. In some examples, PID delivery command 460 at time k may be governed by the equation: $PID(k) = K_P * Err(k) + K_D * dErr(k)/dt + K_I * Int(k)$, where $Err(k)$ represents the difference between the patient's current (e.g., most recent) glucose measurement at time k and a target glucose level and $Int(k)$ represents the integral term governed by the equation $Int(k) = Int(k-1) + c_1 * Err(k)$, where $c_1$ is a constant.

In some examples, the closed-loop PID gain coefficients ($K_P$, $K_I$, $K_D$) and potentially other control parameters (e.g., time constants or the like) may be calculated or otherwise determined using historical insulin delivery data. The historical insulin delivery data may include, but is not limited to, a type of insulin delivered, bolus amounts, timings of previous boluses, correction bolus information, glycemic response, current (historical) glucose levels, reference glucose levels, meal indications, patient-input events (e.g., exercise), or other information related to insulin delivery.

In some examples, one or more patient-specific parameters may be utilized to compensate, correct, or otherwise adjust the PID gain coefficients to account for various operating conditions experienced and/or exhibited by infusion device 202. The one or more patient-specific parameters may include, for example, an insulin sensitivity factor, a daily insulin requirement, an insulin limit, a reference basal rate, a reference fasting glucose, an active insulin action duration, pharmacodynamic time constants, or the like.

The PID gain coefficients may be stored in storage components 270. In some examples, storage components 270 may include a plurality of registers each associated with a respective control parameter for the PID control. For example, a first parameter register may store the target glucose level and be accessed by or otherwise associated with summation block 410, and similarly, a second parameter register accessed by proportional gain block 416 may store the proportional gain coefficient, a third parameter register accessed by integration gain block 418 may store the integration gain coefficient, and a fourth parameter register accessed by derivative gain block 422 may store the derivative gain coefficient. Various implementation details pertaining to closed-loop PID control and determining gain coefficients are described in greater detail in commonly assigned U.S. Pat. No. 7,402,153, which is incorporated by reference in its entirety.

Closed-loop control system 400 also may include an insulin feedback (IFB) portion 404. IFB portion 404 may be configured to adjust the value of PID delivery command 460 to compensate for insulin already delivered to the patient, e.g., insulin on board (JOB). By compensating for JOB, insulin over-delivery may be curtailed or avoided. IFB portion 404 includes summation block 442 configured to determine a difference between the value of PID delivery command 460 and insulin feedback (IFB) term 440 to determine bolus compensated delivery command 450. Motor control module 212, in response to a signal indicative of the bolus compensated delivery command 450, may operate the motor 232 to deliver insulin to the patient to regulate the glucose level toward the target glucose level. In this way, closed-loop control system 400 may reduce the difference between a subsequently measured glucose level and the target glucose level in a manner that accounts for the amount of IOB that is yet to be metabolized by the patient.

In some examples, closed-loop control system 400 may be configured to determine IFB term 440 as a function of historical insulin delivery data using pharmacokinetic models to estimate the amount of active insulin or JOB. For example, historical insulin delivery data, including amounts and timings of previous boluses (e.g., meal boluses, correction boluses, autocorrection boluses, manually-initiated boluses, and/or the like), may be stored in one or more storage components 270. Pharmacokinetic models may be used to determine, based on the timings and amounts of previous boluses, an amount of active insulin or IOB remaining in the subcutaneous, plasma, and effect site compartments. The determined amount may be equal to, proportional to, or mathematically associated with IFB term 440. As one example, the amount of active insulin remaining in the respective compartments at a sampling time k may be governed by the following Equations (1), (2), and (3):

$$I_S(k) = a_{11} \cdot I_S(k-1) + b_I \cdot I_D(k); \tag{1}$$

$$I_P(k) = a_{21} \cdot I_S(k-1) + a_{22} \cdot I_P(k-1) + b_2 \cdot I_D(k); \text{ and} \tag{2}$$

$$I_E(k) = a_{31} \cdot I_S(k-1) + a_{32} \cdot I_P(k-1) + a_{33} \cdot I_E(k-1) + b_3 \cdot I_D(k), \tag{3}$$

where $I_S$ is the insulin in the subcutaneous compartment, $I_P$ is the insulin in the plasma compartment, $I_E$ is the effective insulin compartment, and $I_D(k)$ represents the amount of a bolus dosage delivered at time k (excluding any basal dosage delivery), where the remaining a and b terms represent numerical constants, the derivation of which are described in greater detail in, for example, commonly assigned United States Patent Application Publication Nos.: 2014/0066887 and 2014/0066889, the entire contents of which are incorporated herein by reference in their entirety. In examples in which insulin delivery is suspended at time k, $I_D(k) = 0$. The amounts of IOB remaining in the subcutaneous, plasma, and effective insulin compartments may be added or otherwise combined to arrive at cumulative insulin feedback term 440 at time k using the following equation: $IFB(k) = \gamma_1 \cdot I_S(k) + \gamma_2 \cdot I_P(k) + \gamma_3 \cdot I_E(k)$, where $\gamma_1$, $\gamma_2$, or $\gamma_3$ represent numerical constants, the derivation of which are described in greater detail in, for example, United States Patent Application Publication Nos.: 2014/0066887 and 2014/0066889. IFB term 440 may be provided to summation block 442 and subtracted from the value of PID delivery command 460 at time k to produce the basal delivery value of bolus compensated delivery command 450.

In some examples, insulin feedback (IFB) portion 404 may include limiter 464. Limiter 464 may be configured to limit the output of IFB portion 404. For example, constraining the upper limit of compensated delivery command 450 may prevent insulin stacking, avoid over-delivery, or both.

In some examples, an upper limit of limiter 464 may be calculated in a patient-specific manner based on the patient's fasting blood glucose value and the patient's insulin sensitivity. For example, upper limit may be calculated as described in United States Patent Application Publication No. 2014/0066889.

In some examples, limiter 464 may be configured to receive PID delivery command 460, the output of summation block 442, or both, and filter out any closed-loop delivery command values less than $U_{max}$ from inclusion in the $I_D(k)$ term. For example, when closed-loop delivery command 460 and/or the output of summation block 442 is greater than $U_{max}$, the $I_D(k)$ term may subtract $U_{max}$ from the output of summation block 442. In some examples, the output of summation block 442 may be less than zero when IFB term 440 is greater than PID delivery command 460. When this occurs, closed-loop control system 400 may suspend insulin delivery.

While the subject matter is described above in the context of an insulin feedback term calculated using fixed numerical constants for the a and b terms, in other examples, the a and b terms in the insulin feedback equations may be determined in a patient-specific manner to reflect patient-specific pharmacokinetic or pharmacodynamic response. In some examples, a patient-specific IFB term may be dynamically determined and utilized as IFB term 440.

Figure 4:
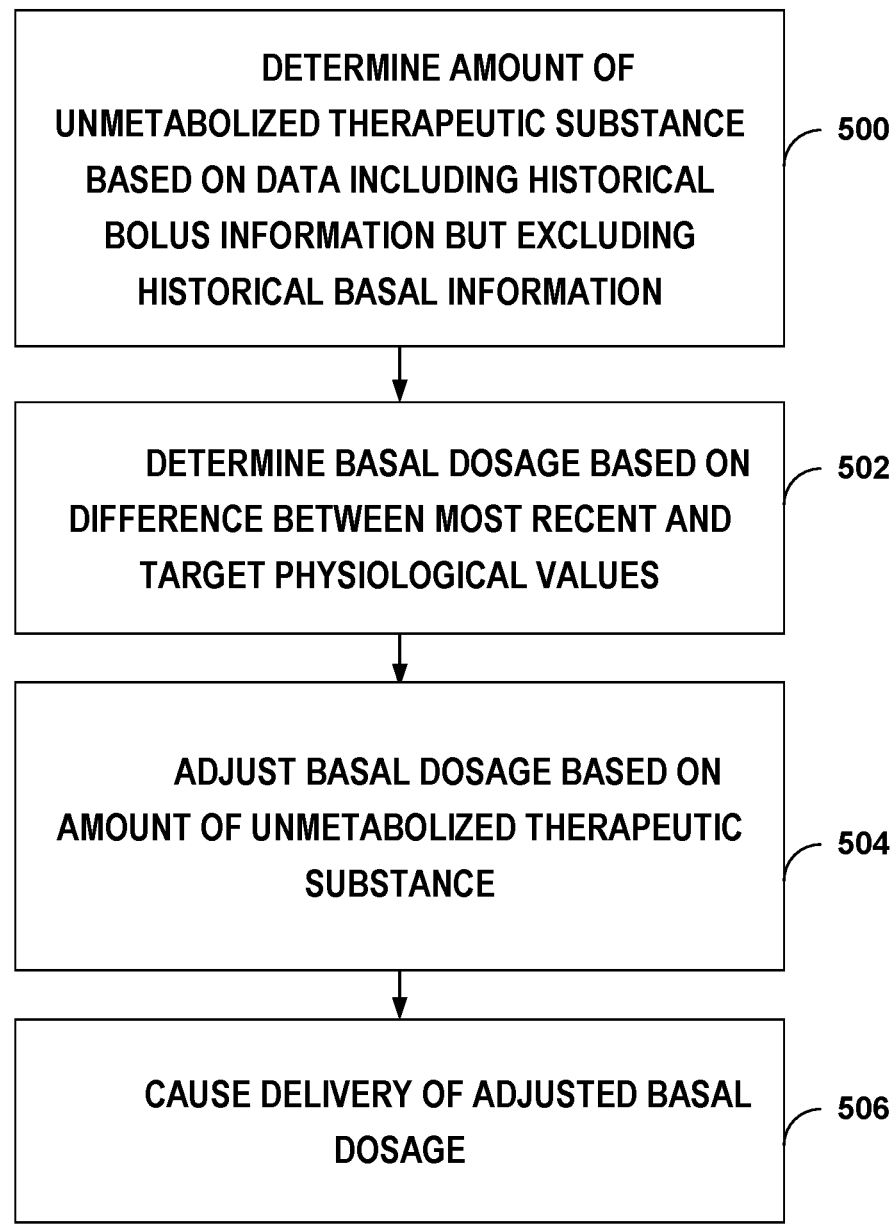
FIG. 4 is a flow diagram illustrating an example process for closed-loop control in steady state conditions.

FIG. 4 is a flow diagram illustrating an example process for closed-loop control in steady-state conditions. Although the techniques illustrated in FIG. 4 are described in reference to systems 100, 200, and/or 400, in some examples, the techniques may be performed using one or more different systems.

The techniques illustrated in FIG. 4 include determining, based on data including historical bolus information but excluding historical basal information, an amount of unmetabolized therapeutic substance in a patient (500). The data may be generated based on filtering historical delivery data to exclude the historical basal information. In some embodiments, the amount of unmetabolized therapeutic substance may be determined based on the data and one or more pharmacokinetic models.

For example, computing device 106 or 206 may obtain insulin delivery data (e.g., from infusion device 102 or 202), which may be maintained as historical insulin delivery data in one or more storage components 270 or some other storage device (e.g., memory). The historical insulin delivery data may be indicative of both amounts and delivery times of bolus dosages, and optionally basal dosages, delivered by infusion device 102 or 202. If the historical insulin delivery data includes information for basal dosages, computing device 106 or 206 may filter the information to generate filtered data. Computing device 106 or 206 may apply one or more pharmacokinetic models to the filtered data to determine the amount of active insulin or IOB.

The techniques illustrated in FIG. 4 also include determining, based on a difference between a most recent (e.g., current) measurement of a physiological condition of the patient and a target value for the physiological condition, a first amount or rate of a basal dosage for delivery to the patient (502). In some embodiments, the first amount or rate of the basal dosage may be determined using a PID closed-loop control process. In some embodiments, an integral path of the PID closed-loop control process may comprise an upper limit equal to a patient-specific maximum amount or rate for the basal dosage.

For example, as described above, PID portion 402 of closed-loop control system 400 may determine uncompensated PID delivery command 460 as a function of the difference between current glucose 406 and target glucose level 408. Determining uncompensated PID delivery command 460 may include limiting, by limiter 462, integral path 415 to an upper limit, such as a patient-specific basal delivery limit ($U_{max}$).

The techniques illustrated in FIG. 4 also include adjusting, based on the amount of unmetabolized therapeutic substance, the first amount or rate of the basal dosage to determine a second amount or rate of the basal dosage (504). For example, computing device 106 or 206 may subtract IFB term 440 from uncompensated PID delivery command 460 to obtain bolus compensated delivery command 450 that accounts for the current estimated amount of active insulin attributable to bolus deliveries.

The techniques illustrated in FIG. 4 also include causing delivery of the second amount or rate of the basal dosage based on communicating the second amount or rate in a delivery command (506). When the first amount or rate of the basal dosage is less than the amount of unmetabolized therapeutic substance, causing delivery of the second amount or rate of the basal dosage may comprise causing suspended delivery of any basal dosages.

For example, if command 450 specifies a positive basal delivery value, computing device 106 or 206 may communicate command 450 to infusion device 102 or 202 (e.g., motor control module 212), and responsive to command 450, infusion device 102 or 202 may deliver a basal dosage to patient 101 or 201. However, if command 450 specifies a non-positive basal delivery value, computing device 106 or 206 may forgo communication of command 450 or otherwise cause basal delivery to be suspended.

The example process of FIG. 4 may be repeated to continually and dynamically update the amount of unmetabolized therapeutic substance attributable to bolus deliveries and correspondingly adjust closed-loop delivery commands.

What is claimed is:

1. A processor-implemented method for closed-loop control in steady-state conditions, the method comprising:
   determining, based on data including historical bolus information but excluding historical basal information, an amount of unmetabolized therapeutic substance in a patient;
   determining, based on a difference between a most recent measurement of a physiological condition of the patient and a target value for the physiological condition, a first amount or rate of a basal dosage for delivery to the patient;
   adjusting, based on the amount of unmetabolized therapeutic substance, the first amount or rate of the basal dosage to determine a second amount or rate of the basal dosage; and
   causing delivery of the second amount or rate of the basal dosage based on communicating the second amount or rate in a delivery command.

2. The method of claim 1, wherein the amount of unmetabolized therapeutic substance is determined based on one or more pharmacokinetic models.

3. The method of claim 1, wherein determining the amount of unmetabolized therapeutic substance comprises generating the data based on filtering historical delivery data to exclude the historical basal information.

4. The method of claim 1, wherein determining the first amount or rate of the basal dosage comprises using a proportional-integral-derivative (PID) closed-loop control process.

5. The method of claim 4, wherein an integral path of the PID closed-loop control process comprises an upper limit equal to a maximum amount or rate for the basal dosage.

6. The method of claim 5, wherein the maximum amount or rate for the basal dosage is patient-specific.

7. The method of claim 1, wherein the first amount or rate of the basal dosage is less than the amount of unmetabolized therapeutic substance, and wherein causing delivery of the second amount or rate of the basal dosage comprises causing suspended delivery of any basal dosages.

8. A system for closed-loop control in steady-state conditions, the system comprising:
   one or more processors; and
   one or more processor-readable storage media storing instructions which, when executed by the one or more processors, cause performance of:
      determining, based on data including historical bolus information but excluding historical basal information, an amount of unmetabolized therapeutic substance in a patient;
      determining, based on a difference between a most recent measurement of a physiological condition of the patient and a target value for the physiological condition, a first amount or rate of a basal dosage for delivery to the patient;
      adjusting, based on the amount of unmetabolized therapeutic substance, the first amount or rate of the basal dosage to determine a second amount or rate of the basal dosage; and
   causing delivery of the second amount or rate of the basal dosage based on communicating the second amount or rate in a delivery command.

9. The system of claim 8, wherein the amount of unmetabolized therapeutic substance is determined based on one or more pharmacokinetic models.

10. The system of claim 8, wherein determining the amount of unmetabolized therapeutic substance comprises generating the data based on filtering historical delivery data to exclude the historical basal information.

11. The system of claim 8, wherein determining the first amount or rate of the basal dosage comprises using a proportional-integral-derivative (PID) closed-loop control process.

12. The system of claim 11, wherein an integral path of the PID closed-loop control process comprises an upper limit equal to a maximum amount or rate for the basal dosage.

13. The system of claim 12, wherein the maximum amount or rate for the basal dosage is patient-specific.

14. The system of claim 8, wherein the first amount or rate of the basal dosage is less than the amount of unmetabolized therapeutic substance, and wherein causing delivery of the second amount or rate of the basal dosage comprises causing suspended delivery of any basal dosages.

15. One or more non-transitory processor-readable storage media storing instructions which, when executed by one or more processors, cause performance of:
   determining, based on data including historical bolus information but excluding historical basal information, an amount of unmetabolized therapeutic substance in a patient;
   determining, based on a difference between a most recent measurement of a physiological condition of the patient and a target value for the physiological condition, a first amount or rate of a basal dosage for delivery to the patient;
   adjusting, based on the amount of unmetabolized therapeutic substance, the first amount or rate of the basal dosage to determine a second amount or rate of the basal dosage; and
   causing delivery of the second amount or rate of the basal dosage based on communicating the second amount or rate in a delivery command.

16. The one or more non-transitory processor-readable storage media of claim 15, wherein the amount of unmetabolized therapeutic substance is determined based on one or more pharmacokinetic models.

17. The one or more non-transitory processor-readable storage media of claim 15, wherein determining the amount of unmetabolized therapeutic substance comprises generating the data based on filtering historical delivery data to exclude the historical basal information.

18. The one or more non-transitory processor-readable storage media of claim 15, wherein determining the first amount or rate of the basal dosage comprises using a proportional-integral-derivative (PID) closed-loop control process.

19. The one or more non-transitory processor-readable storage media of claim 18, wherein an integral path of the PID closed-loop control process comprises an upper limit equal to a maximum amount or rate for the basal dosage.

20. The one or more non-transitory processor-readable storage media of claim 15, wherein the first amount or rate of the basal dosage is less than the amount of unmetabolized therapeutic substance, and wherein causing delivery of the second amount or rate of the basal dosage comprises causing suspended delivery of any basal dosages.

* * * * *